(12) United States Patent
Wei et al.

(10) Patent No.: US 6,284,504 B1
(45) Date of Patent: Sep. 4, 2001

(54) HUMAN DNA LIGASE III

(75) Inventors: Ying-Fei Wei; Guo-Liang Yu, both of Darnestown, MD (US); William A. Haseltine, NW. Washington, DC (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/054,775

(22) Filed: Apr. 3, 1998

Related U.S. Application Data

(60) Division of application No. 08/464,402, filed on Jun. 5, 1995, now Pat. No. 5,858,705, which is a continuation-in-part of application No. PCT/US95/03939, filed on Mar. 31, 1995.

(51) Int. Cl.⁷ .............................. C12N 9/00; C07H 21/04
(52) U.S. Cl. ............................................ 435/183; 536/23.2
(58) Field of Search .......................... 435/183; 536/23.1, 536/23.2, 23.5

(56) References Cited

FOREIGN PATENT DOCUMENTS

WO 90/12101    10/1990   (WO) .

OTHER PUBLICATIONS

Wei, Y.–F. et al., Mol. Cell. Biol., vol. 15, No. 6, pp. 3206–3216, Jun. 1995.*
Amann, E. et al., Gene, vol. 69, pp. 301–315, 1988.*
Tomkinson et al. DNA ligase III is the major high molecular weight DNA joining activity in SV40–transformed human fibroblasts: normal levels of DNA ligase III activity in Bloom syndrome cells. Nucleic Acid Research, vol.21, No.23, pp. 5425–5430, 1993.
Caldecott et al. An interaction between the mammalian DNA repair protein XRCC1 and DNA ligase III. Molecular and Cell Biology. Vol.14, No. 1, pp. 68–76. 1994.
Tomkinson, et al. Three distinct DNA ligases in mammalian cells. The Journal of Biological Chemistry. vol.266, No. 32, pp. 21728–21735. 1991.
Auffray, et al. Partial cDNA sequence in EST–STS database, Accession No. Z45685. 1994.
Auffray, et al. Partial cDNA sequence in EST–STS database, Accession No. T95824. 1995.
Auffray, et al. Partial cDNA sequence in EST–STS database, Accession No. D15404, 1995.
Auffray, et al. Partial cDNA sequence in EST–STS database, Accession No. F07530, 1995.
Auffray, et al. Partial cDNA sequence in EST–STS database, Accession No. F00233, 1995.
Hillier, et al. Partial cDNA sequence in STS–EST database, Accession No. T95919. 1995.
Clark, et al. Beta–centractin: characterization and distribution of a new member of the centractin family of actin–related proteins. Molecular Biology of the Cell. vol.5, No.12, pp. 1301–1310. 1994.
Wang, Y. et al., J. Biol. Chem., vol. 269, No. 5, pp. 31923–31928, Dec. 1994.*
Studier, F. et al., Meth. Enzymol., vol. 185, pp. 60–89, 1990.*

* cited by examiner

*Primary Examiner*—Ponnathapu Achutamurthy
*Assistant Examiner*—Peter P. Tung
(74) *Attorney, Agent, or Firm*—Human Genome Sciences Inc.

(57) ABSTRACT

A human DNA Ligase III polypeptide and DNA (RNA) encoding such polypeptide and a procedure for producing such polypeptide by recombinant techniques is disclosed. Also disclosed are methods for utilizing such polypeptide via gene therapy for the treatment of disorders associated with a defect in DNA Ligase III. Antagonists against such polypeptides and their use as a therapeutic to destroy unwanted cells are also disclosed. Diagnostic assays to detect mutant DNA Ligase III genes are also disclosed.

22 Claims, 10 Drawing Sheets

Figure 1A

```
1    CCACGCGGTCCGGGCAGCCTGTATGAGCAAGTGCCGAGCCTACGGTGAGCGCCGAGCCGG    60
61   AGAGGCAGCTATATGTCTTTGGCTTTCAAGATCTTCTTTCCACAAACCCTCCGTGCACTC   120
121  AGCCGAAAAGAACTGTGCCCTATTCCGAAAACATCACTGGCGTGATGTAAGACAATTCAGC   180
181  CAGTGGTCAGAAACAGATCTGCTTCATGGACATCCCCTCTTCCTGAGAAGAAAGCCTGTT   240
241  CTATCATTCCAGGGAAGCCATCTAAGATCAAGTGCCACCTACCTTGTTTTCTTGCCAGGG   300
301  TTGCATGTGGGACTCTGCAGTGGCCCCTGTGAGATGGCTGAGCAACGGTTCTGTGTGGAC   360
1                                          M  A  E  Q  R  F  C  V  D     9
361  TATGCCAAGCGTGGCACAGCTGGCTGCAAAAATGCAAGGAAAAGATTGTGAAGGGCGTA   420
10    Y  A  K  R  G  T  A  G  C  K  K  C  K  E  K  I  V  K  G  V         29
```

Figure 1B

```
421  TGCCGAATTGGCAAAGTGGTGCCCAATCCCTTCTCAGAGTCTGGGGGTGATATGAAAGAG  480
30    C   R   I   G   K   V   V   P   N   P   F   S   E   S   G   G   D   M   K   E   49

481  TGGTACCACACATTAAATGCATGTTTGAGAAACTAGAGCGGGCCCGGGCCACCAAAAAAA  540
50    W   Y   H   H   I   K   C   M   F   E   K   L   E   R   A   R   A   T   K   K   69

541  ATCGAGGACCTCACAGAGCTGGAAGGCTGGGAAGAGCTGGAAGATAATGAGAAGGAACAG  600
70    I   E   D   L   T   E   L   E   G   W   E   E   L   E   D   N   E   K   E   Q   89

601  ATAACCCAGCACATTGCAGATCTGTCTTCTAAGGCAGCAGGTACACCAAAGAAGAAAGCT  660
90    I   T   Q   H   I   A   D   L   S   S   K   A   A   G   T   P   K   K   K   A   109

661  GTTGTCCAGGCTAAGTTGACAACCACTGGCCAGGTGACTTCTCCAGTGAAAGGCGCCTCA  720
110   V   V   Q   A   K   L   T   T   T   G   Q   V   T   S   P   V   K   G   A   S   129

721  TTTGTCACCAGTACCAATCCCCGGAAATTTCTGGCTTTTCAGCCAAGCCCAACAACTCT  780
130   F   V   T   S   T   N   P   R   K   F   S   G   F   S   A   K   P   N   N   S   149
```

Figure 1C

```
781   GGGGAAGCCCCCTCGAGCCCCCCTAAGAGAAGTCTGTCTTCAAGCAAATGTGACCCC   840
150   G  E  A  P  S  S  P  T  P  K  R  S  L  S  S  S  K  C  D  P   169

841   AGGCATAAGGACTGTCTGCTACGGGAGTTTCGAAAGTTATGCGCCATGGTGGCCGATAAT   900
170   R  H  K  D  C  L  L  R  E  F  R  K  L  C  A  M  V  A  D  N   189

901   CCTAGCTACAACACGAAGACCCAGATCATCCAGGACTTCCTTCGGAAAGGCTCAGCAGGA   960
190   P  S  Y  N  T  K  T  Q  I  I  Q  D  F  L  R  K  G  S  A  G   209

961   GATGGTTTCCACGGTGATGTGTACCTAACACAGTGAAGCTGCTGCCAGGAGTCATTAAG   1020
210   D  G  F  H  G  D  V  Y  L  T  V  K  L  L  L  P  G  V  I  K   229

1021  ACTGTTTACAACTTGAACGATAAGCAGATTGTGAAGCTTTTCAGTCGCATTTTTAACTGC   1080
230   T  V  Y  N  L  N  D  K  Q  I  V  K  L  F  S  R  I  F  N  C   249

1081  AACCCAGATGATATGGCACGGGACCTAGAGCAGGGTGACGTGTCAGAGACAATCAGAGTC   1140
250   N  P  D  D  M  A  R  D  L  E  Q  G  D  V  S  E  T  I  R  V   269
```

Figure 1D

```
1141  TTCTTTGAGCAGAGCAAGTCTTTCCCCCCAGCTGCCAAGAGCCTCCTTACCATCCAGGAA  1200
270    F  F  E  Q  S  K  S  F  P  P  A  A  K  S  L  L  T  I  Q  E   289

1201  GTGGATGAGTTCCTTCTGCGGCTGTCCAAGCTCACCAAGGAGGATGAGCAGCAACAGGCC  1260
290    V  D  E  F  L  L  R  L  S  K  L  T  K  E  D  E  Q  Q  Q  A   309

1261  CTACAGGACATTGCCTCCAGGTGTACAGCCAATGACCTTAAATGCATCATCAGGTTGATC  1320
310    L  Q  D  I  A  S  R  C  T  A  N  D  L  K  C  I  I  R  L  I   329

1321  AAACATGATCTGAAGATGAACTCAGGTGCAAAACATGTGTTAGACGCCCTTGACCCCAAT  1380
330    K  H  D  L  K  M  N  S  G  A  K  H  V  L  D  A  L  D  P  N   349

1381  GCCTATGAAGCCTTCAAAGCCTCGCGCAACCTGCAGGATGTGGTGGAGCGGGTCCTTCAC  1440
350    A  Y  E  A  F  K  A  S  R  N  L  Q  D  V  V  E  R  V  L  H   369

1441  AACGCGCAGGAGGTGGAGAAGGAGCCGGGCCAGAGACGGAGGGCTCTGAGCGTCCAGGCCTCG  1500
370    N  A  Q  E  V  E  K  E  P  G  Q  R  R  R  A  L  S  V  Q  A  S   389
```

Figure 1E

```
1501 CTGATGACACCTGTGCAGCCCATGTTGGCGGAGGCCTGCAAGTCCGTTGAGTATGCAATG 1560
 390  L  M  T  P  V  Q  P  M  L  A  E  A  C  K  S  V  E  Y  A  M  409

1561 AAGAAATGTCCCAATGGCATGTTCTCTGAGATCAAGTACGATGGAGAGCGAGTCCAGGTG 1620
 410  K  K  C  P  N  G  M  F  S  E  I  K  Y  D  G  E  R  V  Q  V  429
                                    →  ‾‾‾‾‾‾‾‾‾‾‾‾‾‾‾‾‾‾

1621 CATAAGAATGGAGACCACTTCAGCTACTTCAGCCGCAGTCTCAAGCCCGTCCTTCCTCAC 1680
 430  H  K  N  G  D  H  F  S  Y  F  S  R  S  L  K  P  V  L  P  H  449

1681 AAGGTGGCCCACTTTAAGGACTACATTCCCCAGGCTTTTCCTGGGGGCCACAGCATGATC 1740
 450  K  V  A  H  F  K  D  Y  I  P  Q  A  F  P  G  G  H  S  M  I  469

1741 TTGGATTCTGAAGTGCTTCTGATTGACAACAAGACAGGCAAACCACTGCCCTTTGGGACT 1800
 470  L  D  S  E  V  L  L  I  D  N  K  T  G  K  P  L  P  F  G  T  489

1801 CTGGGAGTACACAAGAAAGCAGCCTTCCAGGATGCTAATGTCTGCCTGTTTGTTTTTGAT 1860
 490  L  G  V  H  K  K  A  A  F  Q  D  A  N  V  C  L  F  V  F  D  509
```

Figure 1F

```
1861  TGTATCTACTTTAATGATGTCAGCTTGATGGACAGACCTCTGTGTGAGCGGGAAGTTT  1920
 510   C  I  Y  F  N  D  V  S  L  M  D  R  P  L  C  E  R  R  K  F   529

1921  CTTCATGACAACATGGTTGAAATTCCAAACCGGATCATGTTCTCAGAAATGAAGCGAGTC  1980
 530   L  H  D  N  M  V  E  I  P  N  R  I  M  F  S  E  M  K  R  V   549

1981  ACAAAAGCTTTGGACTTGGCTGACATGATAACCCGGGTGATCCAGGAGGATTGGAGGGG   2040
 550   T  K  A  L  D  L  A  D  M  I  T  R  V  I  Q  E  G  L  E  G   569

2041  CTGGTGCTGAAGGATGTGAAGGGTACATATGAGCCTGGAAAGCGGCACTGGCTGAAAGTG  2100
 570   L  V  L  K  D  V  K  G  T  Y  E  P  G  K  R  H  W  L  K  V   589

2101  AAGAAAGACTATTTGAACGAGGGCGCCATGGCCGACACAGCTGACCTGGTGGTCCTTGGA  2160
 590   K  K  D  Y  L  N  E  G  A  M  A  D  T  A  D  L  V  V  L  G   609

2161  GCCTTCTATGGGCAAGGGAGCAAAGGCGGCATGATGTCAATCTTCCTCATGGGCTGCTAC  2220
 610   A  F  Y  G  Q  G  S  K  G  G  M  M  S  I  F  L  M  G  C  Y   629
```

Figure 1G

```
2221  GACCCTGCCTGGCAGCCAGAAGTGGTGCACAGTCACCAAGTGTGCAGGAGGCCATGATGATGCC  2280
630    D   P   G   S   Q   K   W   C   T   V   T   K   C   A   G   G   H   D   D   A    649

2281  ACGCTTGCCCGCCTGCAGAATGAACTAGACATGGTGAAGATCAGCAAGGACCCCAGCAAA  2340
650    T   L   A   R   L   Q   N   E   L   D   M   V   K   I   S   K   D   P   S   K    669

2341  ATACCCAGCTGGTTGAAGGTCAACAAGATCTACTATCCTGACTTCATCGTCCCAGACCCA  2400
670    I   P   S   W   L   K   V   N   K   I   Y   Y   P   D   F   I   V   P   D   P    689

2401  AAGAAAGCTGCCGTGTGTGGGAGATCACAGGGGCTGAATTCTCCAAATCGGAGGCTCATACA  2460
690    K   K   A   A   V   W   E   I   T   G   A   E   F   S   K   S   E   A   H   T    709

2461  GCTGACGGGATCTCCATCCGATTCCCTGCTGCACCCGAATCCGAGATGATAAGGACTGG  2520
710    A   D   G   I   S   I   R   F   P   R   C   T   R   I   R   D   D   K   D   W    729

2521  AAATCTGCCACTAACCTTCCCCAACTCAAGGAACTGTACCAGTTGTCCAAGGAGAAGGCA  2580
730    K   S   A   T   N   L   P   Q   L   K   E   L   Y   Q   L   S   K   E   K   A    749
```

Figure 1H

```
2581 GACTTCACTGTAGTGGCTGGAGATGAGGGGAGCTCCACTACAGGGGTAGCAGTGAAGAG 2640
 750  D   F   T   V   V   A   G   D   E   G   S   S   T   T   G   G   S   S   E   E    769

2641 AATAAGGGTCCCTCAGGGTCTGCTGTGTCCCGCAAGGCCCCCAGCAAGCCCTCAGCCAGT 2700
 770  N   K   G   P   S   G   S   A   V   S   R   K   A   P   S   K   P   S   A   S    789

2701 ACCAAGAAAGCAGAAGGGAAGCTGAGTAACTCCAACAGCAAAGATGGCAACATGCAGACT 2760
 790  T   K   K   A   E   G   K   L   S   N   S   N   S   K   D   G   N   M   Q   T    809

2761 GCAAAGCCTTCCGCTATGAAGGTGGGGGAGAAGCTGGCCACAAAGTCTTCTCCAGTGAAA 2820
 810  A   K   P   S   A   M   K   V   G   E   K   L   A   T   K   S   S   P   V   K    829

2821 GTAGGGGAGAAGCGGAAAGCTGCTGATGAGACGCTGTGCCAAACAAAGGTATTGCTGGAC 2880
 830  V   G   E   K   R   K   A   A   D   E   T   L   C   Q   T   K   V   L   L   D    849

2881 ATCTTCACTGGGGTGCGGCTTTACTTGCCACCCTCCACACCAGACTTCAGCCGTCTCAGA 2940
 850  I   F   T   G   V   R   L   Y   L   P   P   S   T   P   D   F   S   R   L   R    869
```

Figure 1I

```
2941  CGCTACTTTGTGGCATTCGACGGGGACCTGGTACAGGAATTTGATATGACTTCAGCCACG  3000
 870   R  Y  F  V  A  F  D  G  D  L  V  Q  E  F  D  M  T  S  A  T   889

3001  CACGTGCTGGGTAGCAGGAGACAAGAACCCTGCGGCCCAGCAGGTCTCCCCAGAGTGGATT  3060
 890   H  V  L  G  S  R  D  K  N  P  A  A  Q  Q  V  S  P  E  W  I   909

3061  TGGGCATGTATCCGGAAAACGGAGACTGGTAGCTCCCTGCTAGGTTTGCTGTCTTCCCTCT  3120
 910   W  A  C  I  R  K  R  R  L  V  A  P  C  *                     923

3121  CCCTCAGGCCATACTCTCCTTTACCATACTATTGGACTGGACTCAGGCTGGAGGCAGATA  3180

3181  GACACAGTATAGGGGGAATGGGCTTGCTTCTCCCAAACCCACCAGTTCTCCACTGTCTCT  3240

3241  TCTGGACCAGGAATTAGTTGCTGTGTGGGTGCCACAGCTGAAGTCAGTTTGTCTTGCTGGTT  3300

3301  TAAATAGATCTTTCAGAGCTGGGTGCTGGGTTTGCCATCTTTTGTTTTCTTTGAAAAGC  3360
```

Figure 1J

3361 AGCTTAGTTACCCTTTTTATAAATAAATATCTTGCAGTTAAAAAAAAAAAAAA 3417

HUMAN DNA LIGASE III

This application is a divisional of U.S. application Ser. No. 08/464,402 filed Jun. 5, 1995, now U.S. Pat. No. 5,858,705, which is a continuation-in-part of PCT/US95/03939 filed Mar. 31, 1995.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as Human DNA Ligase III. The invention also relates to inhibiting the action of such polypeptides.

DNA strand breaks and gaps are generated transiently during replication, repair and recombination. In mammalian cell nuclei, rejoining of such strand breaks depends on several different DNA polymerases and DNA ligase enzymes.

The mechanism for joining of DNA strand interruptions by DNA ligase enzymes has been widely described. The reaction is initiated by the formation of a covalent enzyme-adenylate complex. Mammalian and viral DNA ligase enzymes employ ATP as cofactor, whereas bacterial DNA ligase enzymes use NAD to generate the adenylyl group. The ATP is cleaved to AMP and pyrophosphate with the adenylyl residue linked by a phosphoramidate bond to the $\epsilon$-amino group of a specific lysine residue at the active site of the protein (Gumport, R. I., et al., *PNAS*, 68:2559–63 (1971)). Reactivated AMP residue of the DNA ligase-adenylate intermediate is transferred to the 5' phosphate terminus of a single strand break in double stranded DNA to generate a covalent DNA-AMP complex with a 5'-5' phosphoanhydride bond. This reaction intermediate has also been isolated for microbial and mammalian DNA ligase enzymes, but is more short lived than the adenylylated enzyme. In the final step of DNA ligation, unadenylylated DNA ligase enzymes required for the generation of a phosphodiester bond catalyze displacement of the AMP residue through attack by the adjacent 3'-hydroxyl group on the adenylylated site.

The occurrence of three different DNA ligase enzymes, DNA Ligase I, II and III, was established previously by biochemical and immunological characterization of purified enzymes (Tomkinson, A. E. et al., *J. Biol. Chem.*, 266:21728–21735 (1991) and Roberts, E., et al., *J. Biol. Chem.*, 269:3789–3792 (1994)). However, the inter-relationship between these proteins was unclear as a cDNA clone has only been available for DNA Ligase I, the major enzyme of this type in proliferating cells (Barnes, D. E., et al., *PNAS USA*, 87:6679–6683 (1990)). The main function of DNA Ligase I appears to be the joining of Okazaki fragments during lagging-strand DNA replication (Waga, S., et al., *J. Biol. Chem.* 269:10923–10934 (1994); Li, C., et al., *Nucl. Acids Res.*, 22:632–638 (1994); and Prigent, C., et al., *Mol. Cell. Biol.*, 14:310–317 (1994)).

A full-length human cDNA encoding DNA Ligase I has been obtained by functional complementation of a *S. cereviasiae* cdc9 temperature-sensitive DNA ligase mutant (Barker, D. G., *Eur. J. Biochem.*, 162:659–67 (1987)). The full-length cDNA encodes a 102-kDa protein of 919 amino acid residues. There is no marked sequence homology to other known proteins except for microbial DNA ligase enzymes. The active site lysine residue is located at position 568. It also effectively seals single-strand breaks in DNA and joins restriction enzyme DNA fragments with staggered ends. The enzyme is also able to catalyze blunt-end joining of DNA. DNA Ligase I can join oligo (dT) molecules hydrogen-bonded to poly (dA), but the enzyme differs from T4 DNA Ligase II and III in being unable to ligate oligo (dT) with a poly (rA) complementary strand.

Human DNA Ligase III is more firmly associated with the cell nuclei. This enzyme is a labile protein, which is rapidly inactivated at 42° C. DNA Ligase III resembles other eukaryotic DNA Ligase enzymes in requiring ATP as cofactor, but the enzyme differs from DNA Ligase I in having a higher association for ATP. DNA Ligase III catalyzes the formation of phosphodiester bonds with an oligo (dT) • poly (rA) substrate, but not with an oligo (rA) • poly (dT) substrate, so it differs completely from DNA Ligase I in this regard (Arrand, J. E. et al., *J. Biol. Chem.*, 261:9079–82 (1986)).

DNA Ligase III repairs single strand breaks in DNA efficiently, but it is unable to perform either blunt-end joining or AMP-dependent relaxation of super-coiled DNA (Elder, R. H. et al., *Eur. J. Biochem.*, 203:53–58 (1992)).

Clues as to the physiological role of DNA Ligase III have come from its physical interaction in a high salt-resistant complex with another nuclear protein, the XRCC1 gene product (Caldecott, K. W., et al., *Mol. Cell. Biol.*, 14:68–76 (1994) and Ljungquist, S., et al., *Mutat. Res.*, 314:177–186 (1994)). The XRCC1 gene encodes a 70 kDa protein, that by itself does not appear to join DNA strand breaks (Caldecott, K. W., et al., *Mol. Cell. Biol.*, 14:68–76 (1994); Ljungquist, S., et al., *Mutat. Res.*, 314:177–186 (1994) and Thompson, L. H., et al., *Mol. Cell. Biol.*, 10:6160–6171 (1990)). However, mutant rodent cells deficient in XRCC1 protein exhibit reduced DNA Ligase III activity, defective strand break repair, an anomalously high level of sister chromatid exchanges, are hyper-sensitive to simple alkylating agents and ionizing radiation, and have an altered mutation spectrum after exposure to ethyl methanesulfonate (Caldecott, K. W., et al., *Mol. Cell. Biol.*, 14:68–76 (1994); Ljungquist, S., et al., *Mutat. Res.*, 314:177–186 (1994); Thompson, L. H., et al., *Mol. Cell. Biol.*, 10:6160–6171 (1990); and Op het Veld, C. W., et al., *Cancer Res.*, 54:3001–3006 (1994)). These data indicate that XRCC1 mutant cells are defective in base excision-repair, and strongly suggest that both DNA Ligase III and XRCC1 are active in this process (Dianov, G., and Lindahl, T., *Curr. Biol.*, 4:1069–1076 (1994)).

A purified mammalian protein fraction active in repair and recombination processes in vitro was shown to contain a ligase with the properties of Human DNA Ligase III, but no detectable amounts of Human DNA Ligase I (Jessberger, R., et al.,*J. Biol. Chem.*, 268:15070–15079 (1993)). The role of the distinct enzyme, DNA Ligase II, remains unclear, although an observed increase in DNA Ligase II activity during meiotic prophase suggests a role in meiotic recombination (Higashitani, A., et al., *Cell Struct. Funct.*, 15:67–72 (1990)). Comparison of $^{32}$P-adenylylated DNA Ligase II and III by partial or complete proteolytic cleavage patterns indicated that these two enzymes share extensive amino acid sequence similarity or identity flanking their active sites, but that they are quite different from DNA Ligase I (Roberts, E., et al., *J. Biol. Chem.*, 269:3789–3792 (1994)). Neither DNA Ligase I, II nor III is exclusively a mitochondrial enzyme.

The polynucleotide of the present invention and polypeptide encoded thereby have been putatively identified as human DNA Ligase III as a result of size, amino acid sequence homology to DNA Ligase II and ability to bind XRCC1 protein. Heretofore, the gene sequence of DNA Ligase III was not known.

In accordance with one aspect of the present invention, there are provided novel mature polypeptides which are human DNA Ligase III, as well as biologically active and diagnostically or therapeutically useful fragments, analogs and derivatives thereof.

In accordance with another aspect of the present invention, there are provided isolated nucleic acid molecules encoding human DNA Ligase III, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptides by recombinant techniques comprising culturing recombinant prokaryotic and/or eukaryotic host cells, containing a human DNA Ligase III nucleic acid sequence, under conditions promoting expression of said protein and subsequent recovery of said protein.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

In accordance with another aspect of the present invention there is provided a method of treating conditions which are related to insufficient human DNA Ligase III activity via gene therapy comprising inserting the DNA Ligase III gene into a patient's cells either in vivo or ex vivo. The gene is expressed in transduced cells and as a result, the protein encoded by the gene may be used therapeutically, for example, to prevent disorders associated with defects in DNA, for example, abnormal cellular proliferation, for example cancers, leukemia and tumors, to treat severe immunosuppression, stunted growth and lymphoma, as well as cellular hypersensitivity to DNA-damaging agents.

In accordance with yet a further aspect of the present invention, there is also provided nucleic acid probes comprising nucleic acid molecules of sufficient length to specifically hybridize to human DNA Ligase III sequences which may be used diagnostically to detect a mutation in the gene encoding DNA Ligase III.

In accordance with yet another aspect of the present invention, there are provided antagonists to such polypeptides, which may be manufactured intracellularly or administered through gene therapy for inhibiting the action of such polypeptides, for example, to target and destroy undesired cells, e.g., cancer cells.

In accordance with still another aspect of the present invention, there are provided diagnostic assays for detecting mutations in the polynucleotide sequences of the present invention for detecting diseases related to a lack of Human DNA Ligase III activity.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–J, collectively, shows the cDNA sequence and the corresponding deduced amino sequence of the DNA Ligase III polypeptide. The standard one letter abbreviation for amino acids is used. The vertical arrow indicates the active site lysine.

In accordance with an aspect of the present invention, there is provided an isolated nucleic acid (polynucleotide) which encodes for the mature polypeptide having the deduced amino acid sequence of FIGS. 1A–J, collectively, (SEQ ID No. 2) or for the mature polypeptide encoded by the cDNA of the clone deposited as ATCC Deposit No. 97052 on Feb. 6, 1995 with the American Tissue Culture Collection, 10801 University Blvd., Manassas, Va. 20110-2209, USA.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

A polynucleotide encoding a polypeptide of the present invention may be obtained from testis, prostate, heart and thymus. The polynucleotide of this invention was discovered in a cDNA library derived from human testis. It is structurally related to the DNA ligase family. It contains an open reading frame encoding a protein of 922 amino acid residues. The protein exhibits the highest degree of homology to vaccine virus DNA ligase with 56% identity and 73% similarity over the entire protein. It is also important that there is a conserved active lysine residue at position 421 which is bordered on either side by a hydrophobic amino acid residue, and the sequence E-KYDG-R is also conserved and is common to enzymes from different sources such as mammalian cells, yeasts, vaccinia virus and bacteriophage T7.

The region flanking the conserved lysine residue is an active site motif that is essential for the formation of an enzyme-adenylate reaction intermediate (Tomkinson, A. E., et al., *PNAS USA*, 88:400–404 (1991)). The conserved lysine residue is indicated by a vertical arrow and the active site motif is underlined in FIGS. 1A–J, collectively. Further a putative zinc finger motif shown at residues 18 to 55 in FIGS. 1A–1L, collectively, is underlined by a broken line. The 100 kDa in vitro translation product of the DNA ligase III cDNA interacts with human XRCC1 protein which is a characteristic of DNA Ligase III (Caldecott, K. W., et al., *Mol. Cell. Biol.*, 14:68–76 (1994)). Histidine-tagged recombinant XRCC1 protein was incubated with [$^{35}$S] methionine-labelled in vitro translation product of the cDNA to allow formation of XRCC1-protein complexes, after which NTA-agarose beads were added to affinity-bind XRCC1-His. The agarose beads were washed to remove non-specifically associated polypeptides prior to elution of XRCC1-His with 200 mM imidazole. XRCC1-his binds the product of the cDNA. Recovery of radiolabeled polypeptides is dependent on addition of XRCC1-His. Approximately 50% of the full length 100 kDa translation product, and as much as 90% of some of the truncated polypeptides, were recovered with XRCC1-His. These results indicate that the cDNA clone encodes a 100 kDa polypeptide.

The longest open reading frame of the cDNA encoding DNA ligase III extends from 73 bp to 3099 bp within the cDNA clone and would encode a polypeptide of 1009 amino acids, approximately 150 kDa molecular mass. The next downstream ATG at 334 bp occurs in a typical translation start consensus and defines an open reading frame of 2766 bp (922 amino acids). The protein produced in this case would be approximately 103 kDa, consistent with both the observed molecular mass of the in vitro translation product and the apparent molecular mass of authentic DNA Ligase III purified from HeLa cells by standard chromatographic procedures. This indicates that this cDNA represents a full length cDNA clone. Furthermore, a 5'-truncated cDNA clone lacking the first 78 bp (and the first ATG codon) produced an in vitro translation product of identical electrophoretic mobility to that encoded by the full length clone, in support of assignment of the ATG at 334 bp as the translation initiation codon.

The DNA Ligase III amino acid sequence shows extensive amino acid homology to Human DNA Ligase I. The DNA Ligase III sequence is identical at 8 of 12 residues flanking the active site lysine of DNA Ligase I, and both contain the minimum active site consensus for all ATP-dependent DNA ligases, -K-DG-R-, (SEQ ID NO:10) with $lys_{421}$ (DNA Ligase III) being the putative active lysine. Although their amino acid sequences are not colinear at optimum alignment, human DNA Ligase I and III differ by 9 amino acids in the size of the region between the two motifs (active lysine and minimum active site motifs).

The 3' flanking motif is located 37 amino acids from the C-terminus of DNA Ligase I, whereas the DNA Ligase III sequence extends a further 195 residues. The C-terminus of the DNA Ligase III shows weak homology to several proteins, including approximately 20% identity to a 144 amino acid sequence within the C-terminal quarter of both human and murine XRCC1.

In their N-terminal regions, DNA Ligase I and III show very limited sequence homology beyond about 30 residues upstream of their active sites, and DNA Ligase I has an extended hydrophilic N-terminal region with no homology to DNA Ligase.

The N-terminal 112 amino acids of the DNA Ligase III cDNA show approximately 30% identity to residues 3 to 107, and also residues 108 to 217, of human poly (ADP ribose) polymerase (PARP). These same two regions contain two evolutionarily conserved zinc finger motifs within the DNA-binding domain of PARP.

The highly conserved motif flanking the 3' boundary of the region of homology between DNA Ligase I and III is unique to ATP-dependent DNA ligases and is not found in the RNA capping enzymes. Similarly to vaccinia virus DNA Ligase, Human DNA Ligase III does not contain the region 2 motif which is present in the capping enzymes, and Human DNA Ligase I (Shuman, S., et al. PNAS USA, in press (1994)).

There is near identity of peptides within the predicted amino acid sequence of the DNA Ligase III cDNA with sequenced tryptic peptides from the 70 kDa bovine DNA Ligase II protein (Wang, Y-C. J., et al., *J. Biol. Chem.*, 269:31923–31928 (1994)). These tryptic peptides span the region between the active site and the conserved DNA Ligase-specific motif, and are also highly homologous to the corresponding region of the vaccinia virus DNA ligase. The sequence $_{411}$-(K)CPNGMFSEIKYDGERVQVH(K)-$_{431}$ (SEQ ID No. 9) in the DNA ligase III cDNA, with $Lys_{421}$, the putative active lysine, is identical to the active site tryptic peptide identified in the purified bovine DNA Ligase II protein and different from that of DNA Ligase I (Tomkinson, A. E., et al., *PNAS USA*, 88:400–404 (1991)).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–J, collectively, (SEQ ID No. 1) or that of the deposited clone or may be a different coding sequence which coding sequence, as a result of the redundancy or degeneracy of the genetic code, encodes the same mature polypeptide as the DNA of FIGS. 1A–J, collectively, (SEQ ID No. 1) or the deposited cDNA.

The polynucleotide which encodes for the mature polypeptide of FIGS. 1A–J, collectively, (SEQ ID No. 2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–J, collectively, (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–J, collectively, (SEQ ID No. 2) or the same mature polypeptide encoded by the cDNA of the deposited clone as well as variants of such polynucleotides which variants encode for a fragment, derivative or analog of the polypeptide of FIGS. 1A–J, collectively, (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–J, collectively, (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or MRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–J, collectively, (SEQ ID NO:1) or the deposited cDNA (s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a DNA Ligase III polypeptide which has the deduced amino acid sequence of FIGS. 1A–J, collectively, (SEQ ID No. 2) or which has the amino acid sequence encoded by the deposited CDNA, as well as fragments, analogs and derivatives of such polypeptide.

The terms "fragment," "derivative" and "analog" when referring to the polypeptide of FIGS. 1A–J, collectively, (SEQ ID No. 2) or that encoded by the deposited cDNA, means a polypeptide which retains essentially the same biological function or activity as such polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–J, collectively, (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, which is employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "gene" means the segment of DNA involved in producing a polypeptide chain; it includes regions preceding and following the coding region (leader and trailer) as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the DNA Ligase III genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DRAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation, initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The DNA Ligase III polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The DNA Ligase III polypeptides and agonists and antagonists which are polypeptides, described below, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CKV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E–86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the DNA Ligase III polypeptide is being expressed intracellularly via gene therapy, it may be used to repair single-strand breaks in DNA which result from DNA-damaging agents, e.g., UV radiation. Several human syndromes result from autosomal recessive inheritance for the DNA ligase gene. These syndromes cause severe immunodeficiency and greatly increases the susceptibility of abnormal cellular differentiation due to the disrepair of DNA while at the cellular level they are characterized by chromosome instability and hypersensitivity to DNA-damaging agents. These syndromes include Fanconi's anemia and Blackfan-diamond anemia.

The polypeptide of the present invention may also be employed to treat severe immunosuppression which is the result of a defect in the DNA Ligase III gene. DNA Ligase III may also be employed to treat stunted growth and lymphoma which result from defective rejoining of DNA.

Chromosome abnormalities in the 17q11-12 region, to which the DNA Ligase III gene has been mapped, are associated with several diseases including several neoplasias. The most common neoplastic chromosomal abnormality in this region is a translocation between chromosomes 15 and 17 seen in acute myeloid leukemia subtype m3 which involves the disruption of the retinoic acid receptor α gene (Chomienne, H., et al., *Nature*, 347:558–561 (1990)). However, chromosomal abnormalities in this region are frequently reported in both acute myeloid and lymphoblastic leukemias and are seen sporadically in several other cancers (Mitelman, F., Catalog of Chromosome Aberrations in Cancer (Fourth Edition), Wiley Liss, New York (1991)). Accordingly, the DNA Ligase III gene and gene product may be employed to treat these neoplasias.

Fragments of the full length Ligase III gene may be used as a hybridization probe for a CDNA library to isolate other genes which have a high sequence similarity to the DNA Ligase III gene or have similar biological activity. Probes of this type have at least 20 bases. Preferably, however, the probes have at least 30 bases and may contain, for example, 50 or more bases. The probe may also be used to identify a cDNA clone corresponding to a full length transcript and a genomic clone or clones that contain the complete DNA Ligase III gene including regulatory and promotor regions, exons, and introns.

An example of a screen comprises isolating the coding region of the DNA Ligase III gene by using the known DNA sequence to synthesize an oligonucleotide probe. Labelled oligonucleotides having a sequence complementary to that of the gene of the present invention are used to screen a library of human CDNA, genomic DNA or mRNA to determine which members of the library the probe hybridizes to.

The polypeptide and/or polynucleotide of the present invention may also be employed in relation to scientific research, synthesis of DNA and for the manufacture of DNA vectors. The polypeptide and/or polynucleotide of the present invention may be sold into the research market. Thus, for example DNA Ligase III may be used for ligation of DNA sequences in vitro in a manner similar to other DNA ligase enzymes of the art.

This invention also provides a method of screening compounds to identify those which enhance or inhibit the DNA-joining reaction catalyzed by human DNA Ligase III. An example of such a method comprises combining ATP, DNA Ligase III and DNA having single-strand breaks with the compound under conditions where the DNA Ligase would normally cleave ATP to AMP and the AMP is transferred to the 5' phosphate terminus of a single strand break in double-stranded DNA to generate a covalent DNA-AMP complex with the single strand break being subsequently repaired. The DNA having the single-strand breaks may be supplied in the above example by mutant cells which are deficient in proteins that are responsible for strand break repair, for example, mutant rodent cells deficient in XRCC1 and the cdc9 *S. Cerevisiae* DNA ligase mutant. The ability of the compound to enhance or block the catalysis of this reaction could then be measured to determine if the compound is an effective agonist or antagonist.

Human DNA Ligase III is produced and functions intracellularly, therefore, any antagonist must be intracellular. Potential antagonists to human DNA Ligase III include antibodies which are produced intracellularly. For example, an antibody identified as antagonizing DNA Ligase III may be produced intracellularly as a single chain antibody by procedures known in the art, such as transforming the appropriate cells with DNA encoding the single chain antibody to prevent the function of human DNA Ligase III.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix— see Lee et al., Nucl. Acids Res., 6:3073 (1979); Cooney et al, Science, 241:456 (1988); and Dervan et al., Science, 251: 1360 (1991)), thereby preventing transcription and the production of DNA Ligase III. The antisense RNA oligonucleotide hybridizes to the mRNA in vivo and blocks translation of the MRNA molecule into the DNA Ligase III (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of DNA Ligase III.

Yet another potential antagonist includes a mutated form, or mutein, of DNA Ligase III which recognizes DNA but does not repair single-strand breaks and, therefore, acts to prevent human DNA Ligase III from functioning.

The antagonists may be employed to target undesired cells, e.g., cancer cells and leukemic cells, since the prevention of DNA Ligase III prevents repair of single-strand breaks in DNA and will eventually result in death of the cell.

The small molecule agonists and antagonists of the present invention may be employed in combination with a suitable pharmaceutical carrier. Such compositions comprise a therapeutically effective amount of the molecule and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

This invention also provides the use of the human DNA Ligase III gene as a diagnostic. For example, some diseases result from inherited defective genes. These genes can be detected by comparing the sequence of the defective gene with that of a normal one. That is, a mutant gene would be associated with hypersensitivity to DNA-damaging agents and an elevated susceptibility to abnormal cell growth, for example, tumors, leukemia and cancer.

Individuals carrying mutations in the human DNA Ligase III gene may be detected at the DNA level by a variety of techniques. Nucleic acids used for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. Deletions or insertions can be detected by a change in size of the amplified product in comparison to the normal genotype. Point mutations can be identified by hybridizing amplified DNA to radiolabeled DNA Ligase III RNA or alternatively, radiolabeled DNA Ligase III antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase protection and S1protection or the chemical cleavage method (e.g., Cotton et al., *PNAS, USA*, 85:4397–4401 (1985)).

Thus, the detection of a specific DNA sequence may be achieved by methods such as hybridization, RNase protection, chemical cleavage, direct DNA sequencing, or the use of restriction enzymes, e.g., restriction fragment length polymorphisms, and Southern blotting of genomic DNA. Also, mutations may be detected by in situ analysis.

In addition, some diseases are a result of, or are characterized by, changes in gene expression which can be detected by changes in the MRNA. Alternatively, the DNA Ligase III gene can be used as a reference to identify individuals expressing a decreased level of DNA Ligase III protein, e.g., by Northern blotting.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the CDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Detailed analysis of 19 individual chromosomes using a combination of fractional length measurements and fluorescent binding combined with high-resolution image analysis indicated that Human DNA Ligase III is located within bands 17q11.2-12.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The gene of the present invention has been mapped to chromosome 13q33-34.

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of DNA Ligase III

The DNA sequence encoding DNA Ligase III, ATCC # 97052, is initially amplified using PCR oligonucleotide primers corresponding to the 5' and 3' end sequences of the processed DNA Ligase III gene. The 5' oligonucleotide primer has the sequence 5° CGC GGATCCATGGCTGAGCAACGGTTCTG 3' (SEQ ID No. 3) contains a Bam HI restriction enzyme site (underlined) followed by 20 nucleotides of DNA Ligase III coding sequence starting from the presumed terminal amino acid of the processed protein codon. The 3' sequence 5' GCG TCTAGACTAGCAGGGAGCTACCAG 3' (SEQ ID No. 4) contains complementary sequences to a XbaI site (underlined) and is followed by 18 nucleotides of DNA Ligase III at C-terminal of DNA Ligase III. The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with Bam HI and Pst I. The amplified sequences are ligated into pQE-9 and inserted in frame with the sequence encoding for the histidine tag and the RBS. The ligation mixture is then used to transform *E. coli* strain M15/rep 4 (Qiagen, Inc.) under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein extract is purified from this solution by chromatography on a Nickel-Chelate column under conditions that allow for tight binding by proteins containing the 6-His tag (Hochuli, E. et al., J. Chromatography 411:177–184 (1984)) and eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2
Cloning and Expression of DNA Ligase III Using the Baculovirus Expression System A DNA sequence encoding full length DNA Ligase III protein, ATCC # 97052, is amplified using PCR oligonucleotide primers corresponding to the 5' and 3' sequences of the gene:

The 5' primer has the sequence 5' CGCGAATCC ATGGCTGAGCAACGGTTCTG 3' (SEQ ID No. 5) and contains a BamHI restriction enzyme site (in bold) followed first by 20 nucleotides of N-terminal sequence (the initiation codon for translation "ATG" is underlined).

The 3' primer has the sequence 5' GCG TCTAGACTAGCAGGGAGCTACCAG 3' (SEQ ID No. 6) and contains the cleavage site for the restriction endonuclease XbaI (in bold) and 18 nucleotides complementary to the C-terminal sequence of the DNA Ligase III gene. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the DNA Ligase III protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E.coli* HB101 cells are then transformed and bacteria identified that contained the plasmid (pBac DNA Ligase III) with the DNA Ligase III gene using the enzymes BamHI and XbaI. The sequence of the cloned fragment is confirmed by DNA sequencing.

5 µg of the plasmid pBac DNA Ligase III was cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac DNA Ligase III are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-DNA Ligase III at a multiplicity of infection (MOI) of 2. Six hours later the medium is removed and replaced with SF900 III medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant DNA Ligase III in COS Cells

The expression of plasmid, DNA Ligase III HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire DNA Ligase III precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, Cell 37:767 (1984)). The infusion of HA tag to the target protein allows detection of the recombinant protein with an antibody that recognizes the HA epitope.

The plasmid construction strategy is described as follows:

The DNA sequence encoding DNA Ligase III, ATCC # 97052, is constructed by PCR using two primers: the 5' primer 5' CGCGAATCCATGGCTGAGCAACGGTTCTG 3' (SEQ ID No. 7) contains an BamHI site (underlined) followed by 20 nucleotides of DNA Ligase III coding sequence starting from the initiation codon; the 3' sequence 5' GCGTCTAGATCAAGCGTAGTCTGGGACGTC GTATGGGTAGCAGGGAGCTACCAGTC 3' (SEQ ID No. 8) contains complementary sequences to an XbaI site (underlined), translation stop codon, HA tag and the last 17 nucleotides of the DNA Ligase III coding sequence (not including the stop codon). Therefore, the PCR product contains an BamHI site, DNA Ligase III coding sequence followed by HA tag fused in frame, a translation termination stop codon next to the HA tag, and an XbaI site. The PCR amplified DNA fragment and the vector, pcDNAI/Amp, are digested with BamHI and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant DNA Ligase III, COS cells are transfected with the expression vector by DEAEDEXTRAN method (J. Sambrook, E. Fritsch, T. Maniatis, Molecular Cloning: A Laboratory Manual, Cold Spring Laboratory Press, (1989)). The expression of the DNA Ligase III HA protein is detected by radiolabeling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression Pattern of DNA Ligase III in Human Tissue

Northern blot analysis may be performed to examine the levels of expression of DNA Ligase III in human tissues. Total cellular RNA samples are isolated with RNAzol™ B system (Biotecx Laboratories, Inc. Houston, Tex.) About 15 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime—3 Prime, Inc. Boulder, Colo.). The filter containing the particular RNA blot is then hybridized with radioactive labeled full length DNA Ligase III gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen. The message RNA for DNA Ligase III is abundant in the testis, prostate, heart, thymus.

EXAMPLE 5

In Vitro Transcription/translation of CDNA Clones

Putative full-length CDNA clone was subcloned as follows: DNA ligase III was subcloned as a Sal I/Not I restriction fragment into the multiple cloning sire of pSPORT (Life Technologies), with the 5' end proximal to the T7 promoter; the DNA ligase III plasmid constructs (1 µg) was linearized with either Not I or Xho I (New England Biolabs), downstream of the cDNA insert, then transcribed and capped at 36° C. for 30 minutes with T7 polymerase and the mCAP RNA capping kit (Stratagene). The reactions were terminated by incubation with 10 units RNase-free DNase at 37° C. for 5 minutes. Following phenol/chloroform extraction and ethanol precipitation, the in vitro transcription products were resuspended in 20 µl 10 mM Tris-HCl/1 mM EDTA, pH 8.0 (TE). The transcript (0 to 5 µl, made up to a final volume of 5 µl with water) was translated in 20 µl rabbit reticulocyte lysate (Amersham) at 30° C. for 90 minutes. In order to radiolabel the product of in vitro translation, reaction was supplemented with 20 µCi [$^{35}$S]methionine (3000 Ci mmol$^{-1}$, Amersham). Translations were terminated by incubation with 5 µl of 400 ml$^{-1}$ RNase A/50 mM EDTA at 37° C. for 15 minutes (30 µl final volume). Samples (5 µl) of translations carried out in the presence of [$^{35}$S]methionine were analyzed by electrophoresis in SDS-7.5% polyacrylamide gels and autoradiography. Non-radiolabeled translation products were assayed for ability to form protein-adenylate complexes after removal of ATP by chromatography through spun 1 ml columns of Sephadex G50 (Pharmacia) equilibrated with TE.

EXAMPLE 6

DNA Ligase Assays

5 µl samples from in vitro translations were adenylylated in reaction mixtures (30 µl) containing 60 mM Tris HCl (pH 8.0), 10 mM MgCl$_2$, 50 µg ml$^{-1}$ BSA, 5 mM DTT and 1 µCi [α-$^{32}$P] ATP (3000 Ci mmol$^{-1}$, Amersham) at 20° C. for 10 minutes and then analyzed by electrophoresis in SDS-7.5% polyacrylamide gels and autoradiography. In order to monitor transfer of [$^{32}$P]AMP from protein-adenylate to a nicked DNA substrate, 5 µl samples from adenylylation reactions were incubated for further time periods with or without the addition of 500 ng non-radiolabeled oligo(dT)$_{16}$-poly(dA), as described previously. The ability to transfer [$^{32}$P]AMP from enzyme-adenylate to the hybrid substrates, oligo(dT)-poly(rA) or oligo(rA)-poly(dT), differentiates DNA ligase I, II and III. However, both these latter substrates were rapidly degraded by an RNase H activity upon incubation in the reticulocyte lysate, even when mixtures were used directly without termination of translation reactions by addition of RNase A.

EXAMPLE 7
Expression of DNA Ligase III via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

Moloney murine leukemia virus is digested and treated with calf intestinal phosphatase. The linear vector is fractionated on agarose gel and purified, using glass beads.

The DNA Ligase III cDNA (see FIG. 1), is isolated and the ends of this fragment are treated with DNA polymerase in order to fill in the recessed ends and create blunt ends.

Equal quantities of the Moloney murine leukemia virus linear backbone and the gene are added together, in the presence of T4 DNA ligase. The resulting mixture is maintained under conditions appropriate for ligation of the two fragments. The ligation mixture was used to transform bacteria HB101, which were then plated onto agar-containing kanamycin for the purpose of confirming that the vector had the DNA Ligase III gene properly inserted.

PE501 packaging cells are grown in tissue culture to confluent density in Dulbecco's Modified Eagles Medium (DMEM) with 10% calf serum (CS), penicillin and streptomycin. The Moloney murine leukemia virus vector containing the gene is then added to the media and the packaging cells are transduced with the vector. The packaging cells now produce infectious viral particles containing the DNA Ligase III gene.

Fresh media is added to the transduced producer cells, and subsequently the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells.

The engineered fibroblasts are then injected into the into a host, for example, a rat, either alone or after having been grown to confluence on cytodex 3 microcarrier beads. The fibroblasts now produce the protein product and the biological actions of DNA Ligase III are conveyed to the host.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence at least 95% identical to amino acid residues 2 to 922 of SEQ ID NO:2, wherein said polypeptide has ligase activity.

2. The isolated polypeptide of claim 1 which comprises an amino acid sequence at least 95% identical to amino acid residues 1 to 922 of SEQ ID NO:2.

3. The polypcptidc of claim 1 which comprises a heterologous polypeptide sequence.

4. A composition comprising the polypeptide of claim 1.

5. An isolated polypepitde produced by the method comprising:
   (a) expressing the polypepitde of claim 1 by a cell; and
   (b) recovering said polypeptide.

6. An isolated polypeptide comprising amino acid residues 2 to 922 of SEQ ID NO:2.

7. The isolated polypeptide of claim 6 which comprises amino acid residues 1 to 922 of SEQ ID NO:2.

8. The polypeptide of claim 6 which comprises a heterologous polypeptide sequence.

9. A composition comprising the polypeptide of claim 6.

10. An isolated polypepitde produced by the method comprising:
    (a) expressing the polypepitde of claim 6 by a cell; and
    (b) recovering said polypeptide.

11. An isolated polypeptide comprising an amino acid sequence at least 95% identical to the mature polypeptide encoded by the human cDNA contained in ATCC Deposit No. 97052, wherein said polypeptide has ligase activity.

12. The isolated polypeptide of claim 11 which comprises an amino acid sequence at least 95% identical to the polypeptide encoded by the human cDNA contained in ATCC Deposit No. 97052, excluding the N-tenninal methionine.

13. The isolated polypeptide of claim 11 which comprises an amino acid sequence at least 95% identical to the polypeptide encoded by the human cDNA contained in ATCC Deposit No. 97052.

14. The polypeptide of claim 11 which comprises a heterologous polypeptide sequence.

15. A composition comprising the polypeptide of claim 11.

16. An isolated polypepitdc produced by the method comprising:
    (a) expressing the polypepitde of claim 11 by a cell; and
    (b) recovering said polypeptide.

17. An isolated polypeptide comprising the amino acid sequence of the mature polypeptide encoded by the human cDNA contained in ATCC Deposit No. 97052.

18. The isolated polypeptide of claim 17 which comprises the amino acid sequence of the polypeptide encoded by the human cDNA contained in ATCC Deposit No. 97052, excluding the N-terminal methionine.

19. The isolated polypeptide of claim 17 which comprises the amino acid sequence of the polypeptide encoded by the human cDNA contained in ATCC Deposit No. 97052.

20. The polypeptide of claim 17 which comprises a heterologous polypeptide sequence.

21. A composition comprising the polypeptide of claim 17.

22. An isolated polypepitde produced by the method comprising:
    (a) expressing the polypepitde of claim 17 by a cell; and
    (b) recovering said polypeptide.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 3417 base pairs
      (B) TYPE: nucleic acid
      (C) STRANDEDNESS: double
      (D) TOPOLOGY: linear (ii) MOLECULE TYPE: protein (xi) SEQUENCE DESCRIPTION: SEQ ID NO: 1:

```
CCACGCGTCC GGCAGCCTGT ATGAGCAAGT GCCGAGGCCT ACGGTGAGCG CCGGAGCCGG      60

AGAGGCAGCT ATATGTCTTT GGCTTTCAAG ATCTTCTTTC CACAAACCCT CCGTGCACTC     120

AGCCGAAAAG AACTGTGCCT ATTCCGAAAA CATCACTGGC GTGATGTAAG ACAATTCAGC     180

CAGTGGTCAG AAACAGATCT GCTTCATGGA CATCCCCTCT TCCTGAGAAG AAAGCCTGTT     240

CTATCATTCC AGGGAAGCCA TCTAAGATCA CGTGCCACCT ACCTTGTTTT CTTGCCAGGG     300

TTGCATGTGG GACTCTGCAG TGGCCCCTGT GAGATGGCTG AGCAACGGTT CTGTGTGGAC     360
```

-continued

```
TATGCCAAGC GTGGCACAGC TGGCTGCAAA AAATGCAAGG AAAAGATTGT GAAGGGCGTA       420

TGCCGAATTG GCAAAGTGGT GCCCAATCCC TTCTCAGAGT CTGGGGGTGA TATGAAAGAG       480

TGGTACCACA TTAAATGCAT GTTTGAGAAA CTAGAGCGGG CCCGGGCCAC CACAAAAAAA       540

ATCGAGGACC TCACAGAGCT GGAAGGCTGG GAAGAGCTGG AAGATAATGA GAAGGAACAG       600

ATAACCCAGC ACATTGCAGA TCTGTCTTCT AAGGCAGCAG GTACACCAAA GAAGAAAGCT       660

GTTGTCCAGG CTAAGTTGAC AACCACTGGC CAGGTGACTT CTCCAGTGAA AGGCGCCTCA       720

TTTGTCACCA GTACCAATCC CCGGAAATTT CTGGCTTTT CAGCCAAGCC CAACAACTCT        780

GGGGAAGCCC CCTCGAGCCC CACCCCTAAG AGAAGTCTGT CTTCAAGCAA ATGTGACCCC       840

AGGCATAAGG ACTGTCTGCT ACGGGAGTTT CGAAAGTTAT GCGCCATGGT GGCCGATAAT       900

CCTAGCTACA ACACGAAGAC CCAGATCATC CAGGACTTCC TTCGGAAAGG CTCAGCAGGA       960

GATGGTTTCC ACGGTGATGT GTACCTAACA GTGAAGCTGC TGCTGCCAGG AGTCATTAAG      1020

ACTGTTTACA ACTTGAACGA TAAGCAGATT GTGAAGCTTT TCAGTCGCAT TTTTAACTGC      1080

AACCCAGATG ATATGGCACG GGACCTAGAG CAGGGTGACG TGTCAGAGAC AATCAGAGTC      1140

TTCTTTGAGC AGAGCAAGTC TTTCCCCCCA GCTGCCAAGA GCCTCCTTAC CATCCAGGAA      1200

GTGGATGAGT TCCTTCTGCG GCTGTCCAAG CTCACCAAGG AGGATGAGCA GCAACAGGCC      1260

CTACAGGACA TTGCCTCCAG GTGTACAGCC AATGACCTTA AATGCATCAT CAGGTTGATC      1320

AAACATGATC TGAAGATGAA CTCAGGTGCA AAACATGTGT TAGACGCCCT TGACCCCAAT      1380

GCCTATGAAG CCTTCAAAGC CTCGCGCAAC CTGCAGGATG TGGTGGAGCG GGTCCTTCAC      1440

AACGCGCAGG AGGTGGAGAA GGAGCCGGGC CAGAGACGAG CTCTGAGCGT CCAGGCCTCG      1500

CTGATGACAC CTGTGCAGCC CATGTTGGCG GAGGCCTGCA AGTCCGTTGA GTATGCAATG      1560

AAGAAATGTC CCAATGGCAT GTTCTCTGAG ATCAAGTACG ATGGAGAGCG AGTCCAGGTG      1620

CATAAGAATG GAGACCACTT CAGCTACTTC AGCCGCAGTC TCAAGCCCGT CCTTCCTCAC      1680

AAGGTGGCCC ACTTTAAGGA CTACATTCCC CAGGCTTTTC CTGGGGGCCA CAGCATGATC      1740

TTGGATTCTG AAGTGCTTCT GATTGACAAC AAGACAGGCA AACCACTGCC CTTTGGGACT      1800

CTGGGAGTAC ACAAGAAAGC AGCCTTCCAG GATGCTAATG TCTGCCTGTT TGTTTTTGAT      1860

TGTATCTACT TTAATGATGT CAGCTTGATG GACAGACCTC TGTGTGAGCG GCGGAAGTTT      1920

CTTCATGACA ACATGGTTGA AATTCCAAAC CGGATCATGT TCTCAGAAAT GAAGCGAGTC      1980

ACAAAAGCTT TGGACTTGGC TGACATGATA ACCCGGGTGA TCCAGGAGGG ATTGGAGGGG      2040

CTGGTGCTGA AGGATGTGAA GGGTACATAT GAGCCTGGGA AGCGGCACTG GCTGAAAGTG      2100

AAGAAAGACT ATTTGAACGA GGGGGCCATG GCCGACACAG CTGACCTGGT GGTCCTTGGA      2160

GCCTTCTATG GGCAAGGGAG CAAAGGCGGC ATGATGTCAA TCTTCCTCAT GGGCTGCTAC      2220

GACCCTGGCA GCCAGAAGTG GTGCACAGTC ACCAAGTGTG CAGGAGGCCA TGATGATGCC      2280

ACGCTTGCCC GCCTGCAGAA TGAACTAGAC ATGGTGAAGA TCAGCAAGGA CCCCAGCAAA      2340

ATACCCAGCT GGTTGAAGGT CAACAAGATC TACTATCCTG ACTTCATCGT CCCAGACCCA      2400

AAGAAAGCTG CCGTGTGGGA GATCACAGGG CTGAATTCT CCAAATCGGA GGCTCATACA       2460

GCTGACGGGA TCTCCATCCG ATTCCCTCGC TGCACCCGAA TCCGAGATGA TAAGGACTGG      2520

AAATCTGCCA CTAACCTTCC CCAACTCAAG GAACTGTACC AGTTGTCCAA GGAGAAGGCA      2580

GACTTCACTG TAGTGGCTGG AGATGAGGGG AGCTCCACTA CAGGGGTAG CAGTGAAGAG       2640

AATAAGGGTC CCTCAGGGTC TGCTGTGTCC CGCAAGGCCC CCAGCAAGCC CTCAGCCAGT      2700

ACCAAGAAAG CAGAAGGGAA GCTGAGTAAC TCCAACAGCA AAGATGGCAA CATGCAGACT      2760
```

```
GCAAAGCCTT CCGCTATGAA GGTGGGGAG AAGCTGGCCA CAAAGTCTTC TCCAGTGAAA    2820

GTAGGGGAGA AGCGGAAAGC TGCTGATGAG ACGCTGTGCC AAACAAAGGT ATTGCTGGAC    2880

ATCTTCACTG GGGTGCGGCT TTACTTGCCA CCCTCCACAC CAGACTTCAG CCGTCTCAGA    2940

CGCTACTTTG TGGCATTCGA CGGGGACCTG GTACAGGAAT TTGATATGAC TTCAGCCACG    3000

CACGTGCTGG GTAGCAGGGA CAAGAACCCT GCGGCCCAGC AGGTCTCCCC AGAGTGGATT    3060

TGGGCATGTA TCCGGAAACG GAGACTGGTA GCTCCCTGCT AGGTTTGCTG TCTTCCCTCT    3120

CCCTCAGGCC ATACTCTCCT TTACCATACT ATTGGACTGG ACTCAGGCTG GAGGCAGATA    3180

GACACAGTAT AGGGGAATG GGCTTGCTTC TCCCAAACCC ACCAGTTCTC CACTGTCTCT    3240

TCTGGACCAG GAATTAGTTG CTGTGGGTGC ACAGCTGAA GTCAGTTTGT CTTGCTGGTT    3300

TAAATAGATC TTTCAGAGCT GGGTGCTGGG TTTGCCATCT TTTTGTTTTC TTTGAAAAGC    3360

AGCTTAGTTA CCCTTTTTAT AAATAAAATA TCTTGCAGTT AAAAAAAAAA AAAAAAA       3417
```

(2) INFORMATION FOR SEQ ID NO: 2:

(i) SEQUENCE CHARACTERISTICS:
    (A) LENGTH: 922 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 2:

```
Met Ala Glu Gln Arg Phe Cys Val Asp Tyr Ala Lys Arg Gly Thr Ala
1               5                   10                  15

Gly Cys Lys Lys Cys Lys Glu Lys Ile Val Lys Gly Val Cys Arg Ile
            20                  25                  30

Gly Lys Val Val Pro Asn Pro Phe Ser Glu Ser Gly Gly Asp Met Lys
        35                  40                  45

Glu Trp Tyr His Ile Lys Cys Met Phe Glu Lys Leu Glu Arg Ala Arg
    50                  55                  60

Ala Thr Thr Lys Lys Ile Glu Asp Leu Thr Glu Leu Glu Gly Trp Glu
65                  70                  75                  80

Glu Leu Glu Asp Asn Glu Lys Glu Gln Ile Thr Gln His Ile Ala Asp
                85                  90                  95

Leu Ser Ser Lys Ala Ala Gly Thr Pro Lys Lys Ala Val Val Gln
            100                 105                 110

Ala Lys Leu Thr Thr Thr Gly Gln Val Thr Ser Pro Val Lys Gly Ala
        115                 120                 125

Ser Phe Val Thr Ser Thr Asn Pro Arg Lys Phe Ser Gly Phe Ser Ala
    130                 135                 140

Lys Pro Asn Asn Ser Gly Glu Ala Pro Ser Ser Pro Thr Pro Lys Arg
145                 150                 155                 160

Ser Leu Ser Ser Ser Lys Cys Asp Pro Arg His Lys Asp Cys Leu Leu
                165                 170                 175

Arg Glu Phe Arg Lys Leu Cys Ala Met Val Ala Asp Asn Pro Ser Tyr
            180                 185                 190

Asn Thr Lys Thr Gln Ile Ile Gln Asp Phe Leu Arg Lys Gly Ser Ala
        195                 200                 205

Gly Asp Gly Phe His Gly Asp Val Tyr Leu Thr Val Lys Leu Leu Leu
    210                 215                 220

Pro Gly Val Ile Lys Thr Val Tyr Asn Leu Asn Asp Lys Gln Ile Val
```

-continued

```
225                 230                 235                 240

Lys Leu Phe Ser Arg Ile Phe Asn Cys Asn Pro Asp Asp Met Ala Arg
                245                 250                 255

Asp Leu Glu Gln Gly Asp Val Ser Glu Thr Ile Arg Val Phe Phe Glu
                260                 265                 270

Gln Ser Lys Ser Phe Pro Pro Ala Ala Lys Ser Leu Leu Thr Ile Gln
                275                 280                 285

Glu Val Asp Glu Phe Leu Leu Arg Leu Ser Lys Leu Thr Lys Glu Asp
                290                 295                 300

Glu Gln Gln Gln Ala Leu Gln Asp Ile Ala Ser Arg Cys Thr Ala Asn
305                 310                 315                 320

Asp Leu Lys Cys Ile Ile Arg Leu Ile Lys His Asp Leu Lys Met Asn
                325                 330                 335

Ser Gly Ala Lys His Val Leu Asp Ala Leu Asp Pro Asn Ala Tyr Glu
                340                 345                 350

Ala Phe Lys Ala Ser Arg Asn Leu Gln Asp Val Val Glu Arg Val Leu
                355                 360                 365

His Asn Ala Gln Glu Val Glu Lys Glu Pro Gly Gln Arg Arg Ala Leu
                370                 375                 380

Ser Val Gln Ala Ser Leu Met Thr Pro Val Gln Pro Met Leu Ala Glu
385                 390                 395                 400

Ala Cys Lys Ser Val Glu Tyr Ala Met Lys Lys Cys Pro Asn Gly Met
                405                 410                 415

Phe Ser Glu Ile Lys Tyr Asp Gly Glu Arg Val Gln Val His Lys Asn
                420                 425                 430

Gly Asp His Phe Ser Tyr Phe Ser Arg Ser Leu Lys Pro Val Leu Pro
                435                 440                 445

His Lys Val Ala His Phe Lys Asp Tyr Ile Pro Gln Ala Phe Pro Gly
                450                 455                 460

Gly His Ser Met Ile Leu Asp Ser Glu Val Leu Leu Ile Asp Asn Lys
465                 470                 475                 480

Thr Gly Lys Pro Leu Pro Phe Gly Thr Leu Gly Val His Lys Lys Ala
                485                 490                 495

Ala Phe Gln Asp Ala Asn Val Cys Leu Phe Val Phe Asp Cys Ile Tyr
                500                 505                 510

Phe Asn Asp Val Ser Leu Met Asp Arg Pro Leu Cys Glu Arg Arg Lys
                515                 520                 525

Phe Leu His Asp Asn Met Val Glu Ile Pro Asn Arg Ile Met Phe Ser
                530                 535                 540

Glu Met Lys Arg Val Thr Lys Ala Leu Asp Leu Ala Asp Met Ile Thr
545                 550                 555                 560

Arg Val Ile Gln Glu Gly Leu Glu Gly Leu Val Leu Lys Asp Val Lys
                565                 570                 575

Gly Thr Tyr Glu Pro Gly Lys Arg His Trp Leu Lys Val Lys Lys Asp
                580                 585                 590

Tyr Leu Asn Glu Gly Ala Met Ala Asp Thr Ala Asp Leu Val Val Leu
                595                 600                 605

Gly Ala Phe Tyr Gly Gln Gly Ser Lys Gly Gly Met Met Ser Ile Phe
                610                 615                 620

Leu Met Gly Cys Tyr Asp Pro Gly Ser Gln Lys Trp Cys Thr Val Thr
625                 630                 635                 640

Lys Cys Ala Gly Gly His Asp Asp Ala Thr Leu Ala Arg Leu Gln Asn
                645                 650                 655
```

```
Glu Leu Asp Met Val Lys Ile Ser Lys Asp Pro Ser Lys Ile Pro Ser
            660                 665                 670

Trp Leu Lys Val Asn Lys Ile Tyr Tyr Pro Asp Phe Ile Val Pro Asp
        675                 680                 685

Pro Lys Lys Ala Ala Val Trp Glu Ile Thr Gly Ala Glu Phe Ser Lys
    690                 695                 700

Ser Glu Ala His Thr Ala Asp Gly Ile Ser Ile Arg Phe Pro Arg Cys
705                 710                 715                 720

Thr Arg Ile Arg Asp Asp Lys Asp Trp Lys Ser Ala Thr Asn Leu Pro
                725                 730                 735

Gln Leu Lys Glu Leu Tyr Gln Leu Ser Lys Glu Lys Ala Asp Phe Thr
            740                 745                 750

Val Val Ala Gly Asp Glu Gly Ser Ser Thr Thr Gly Gly Ser Ser Glu
        755                 760                 765

Glu Asn Lys Gly Pro Ser Gly Ser Ala Val Ser Arg Lys Ala Pro Ser
    770                 775                 780

Lys Pro Ser Ala Ser Thr Lys Lys Ala Glu Gly Lys Leu Ser Asn Ser
785                 790                 795                 800

Asn Ser Lys Asp Gly Asn Met Gln Thr Ala Lys Pro Ser Ala Met Lys
                805                 810                 815

Val Gly Glu Lys Leu Ala Thr Lys Ser Ser Pro Val Lys Val Gly Glu
            820                 825                 830

Lys Arg Lys Ala Ala Asp Glu Thr Leu Cys Gln Thr Lys Val Leu Leu
        835                 840                 845

Asp Ile Phe Thr Gly Val Arg Leu Tyr Leu Pro Pro Ser Thr Pro Asp
850                 855                 860

Phe Ser Arg Leu Arg Arg Tyr Phe Val Ala Phe Asp Gly Asp Leu Val
865                 870                 875                 880

Gln Glu Phe Asp Met Thr Ser Ala Thr His Val Leu Gly Ser Arg Asp
                885                 890                 895

Lys Asn Pro Ala Ala Gln Gln Val Ser Pro Glu Trp Ile Trp Ala Cys
            900                 905                 910

Ile Arg Lys Arg Arg Leu Val Ala Pro Cys
        915                 920

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGCGGATCCA TGGCTGAGCA ACGGTTCTG                                      29

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:
```

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GCGTCTAGAC TAGCAGGGAG CTACCAG                                27
```

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
CGCGAATCCA TGGCTGAGCA ACGGTTCTG                              29
```

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
CGCGAATCCA TGGCTGAGCA ACGGTTCTG                              29
```

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
CGCGAATCCA TGGCTGAGCA ACGGTTCTG                              29
```

(2) INFORMATION FOR SEQ ID NO: 8:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
GCGTCTAGAT CAAGCGTAGT CTGGGACGTC GTATGGGTAG CAGGGAGCTA CCAGTC    56
```

(2) INFORMATION FOR SEQ ID NO: 9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Lys Cys Pro Asn Gly Met Phe Ser Glu Ile Lys Tyr Asp Gly Glu Ar
  1               5                  10                  15
```

-continued

```
Val Gln Val His Lys
            20

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Xaa Lys Xaa Asp Gly Xaa Arg Xaa
1               5
```